(12) United States Patent
Matsumoto

(10) Patent No.: US 6,773,563 B2
(45) Date of Patent: Aug. 10, 2004

(54) ELECTROCHEMICAL SENSOR HAVING A REFERENCE ELECTRODE

(75) Inventor: Toru Matsumoto, Tokyo (JP)

(73) Assignee: NEC Corporation, Tokyo (JP)

( * ) Notice: Subject to any disclaimer, the term of this patent is extended or adjusted under 35 U.S.C. 154(b) by 398 days.

(21) Appl. No.: 09/924,001

(22) Filed: Aug. 8, 2001

(65) Prior Publication Data

US 2002/0029964 A1 Mar. 14, 2002

(30) Foreign Application Priority Data

Aug. 9, 2000 (JP) .......................................... 2000-241223

(51) Int. Cl.[7] ..................... G01N 27/403; G01N 27/327
(52) U.S. Cl. ..................... 204/401; 204/403.1; 204/412
(58) Field of Search ................................. 204/401, 406, 204/412, 403.1, 403.11, 403.14, 435

(56) References Cited

U.S. PATENT DOCUMENTS 5,100,530 A * 3/1992 Dorr et al. .................. 204/406
5,766,432 A * 6/1998 Dunn et al. ................. 204/412
6,299,757 B1 * 10/2001 Feldman et al. ............ 205/775

FOREIGN PATENT DOCUMENTS

| JP | 5-256812 | 10/1993 |
|---|---|---|
| JP | 6-3323 | 1/1994 |

* cited by examiner

Primary Examiner—Kaj K. Olsen
(74) Attorney, Agent, or Firm—McGinn & Gibb, PLLC

(57) ABSTRACT

An electrochemical sensor based on a three-electrode method containing a reference electrode, comprising: A working electrode 2, a counter electrode 3 and a reference electrode 4 formed on an insulating substrate 1; an examining electrode 8 provided to examine an electric potential of the reference electrode 4; a combining layer 20, an immobilized enzyme layer 21 and a diffusion-limiting layer 22 made of a fluororesin provided on voltmeter is provided on these electrodes, between the examining electrode 8 and the reference electrode 4 so that the electric potential of the reference electrode can be examined; to detect an abnormality in the reference electrode immediately after its occurrence, recover a high reliability of measured value by removing the abnormality quickly, make it possible to conduct a continuous measurement for a long time and furthermore try to reduce a running cost.

27 Claims, 10 Drawing Sheets

(a)

(b)

(a)

(b)

(a)

(b)

THE REFERENCE ELECTRODE IN USE WAS DAMAGED AND A NEW REFERENCE ELECTRODE HAS STARTED TO FUNCTION AS A STANDARD ELECTRODE.

(a) 1 mM K₂S  (b) 1 mM KBr  (c) 1 mM KI

——— WITH THE DIFFUSION-LIMITING LAYER
- - - WITHOUT THE DIFFUSION-LIMITING LAYER (a)

(b)

OUTPUT OF THE GLUCOSE SENSOR (a)

NATURAL ELECTRIC POTENTIAL OF THE
REFERENCE ELECTRODE (b)

ELECTROCHEMICAL SENSOR HAVING A REFERENCE ELECTRODE

FIELD OF THE INVENTION

This invention relates to an electrochemical sensor having a working electrode, a counter electrode and a reference electrode.

BACKGROUND OF THE INVENTION

When using a sensor performs an electrochemical measurement, a three-electrode method is widely employed, wherein an electrode group consisting of a working electrode, a counter electrode and a reference electrode is used. As an example of this type of sensor, a biosensor is disclosed in FIGS. 1(a)–1(b) of Japanese Patent Application under Provisional Publication No. 256812/93, wherein a working electrode, a reference electrode and a counter electrode that are molded with platinum are provided on an aminoethanesulfonic insulating substrate. As another example, an electrochemical gas sensor is disclosed in FIGS. 1(a)–1(b) and FIG. 6 of Japanese Patent Application under Provisional Publication No. 3323/94, wherein two sets of a pair of electrode group consisting of a working electrode and a counter electrode are provided for a single reference electrode.

When an electrochemical measurement by the three-electrode method is applied, it is important to confirm that each electrode functions normally before the measurement. Therefore, it is usually required to confirm the normal function of a measuring apparatus by the calibration using a calibration solution. However, in some cases an error in measured value becomes large even if the calibration is conducted. Accuracy of measurement of a sensor is dependent greatly on the characteristic of a reference electrode since a specified electric potential is applied to a working electrode on the basis of the reference electrode in a senor using the reference electrode. However, since the characteristic of the reference electrode changes due to various factors, the electric potential changes and the function as the reference electrode is sometimes greatly damaged. Although an abnormality relating to the senor as a whole apparatus may be confirmed by the calibration of the sensor before measurement, it is usually difficult to detect a delicate change of the electric potential of the reference electrode. Therefore, an accurate value of measurement may not be obtained even after the calibration described above is performed.

In addition, in the light of a convenience of a process and a small sizing of a sensor, a working electrode, a counter electrode and a reference electrode are formed on the same substrate in a normal electrochemical sensor as can be seen in the Provisional Publications described above. Therefore, the whole substrate whereon an electrode group is set has to be replaced when the reference electrode has some troubles even though the working electrode and the counter electrode are functioning normally. When the reference electrode is made of a material which tends to be damaged as compared with that used for the working electrode and the counter electrode, a restriction is imposed on a decrease in a running cost and an extension of a possible continuous measurement time depending on the life of the reference electrode and, therefore, there has still remained a room for improvement in this regard.

SUMMARY OF THE INVENTION

The circumstances mentioned above have led to this invention.

This invention relates to an electrochemical sensor based on a three-electrode method containing a reference electrode and the purpose of this invention is to detect an abnormality in the reference electrode immediately after its occurrence, recover a high reliability of measured value by removing the abnormality quickly, make it possible to conduct a continuous measurement for a long time and furthermore try to reduce a running cost.

This invention by which the problems mentioned above are solved are specified by the followings:

[1] An electrochemical sensor having a working electrode, a counter electrode, and a reference electrode, wherein a means for examining the reference electrode is provided for examining an electric potential of the reference electrode.

[2] The electrochemical sensor as describe in [1], wherein the means for examining the reference electrode comprises having an examining electrode as a standard to measure the electric potential of the reference electrode and a measuring apparatus by which a potential difference between the examining electrode and the reference electrode is measured.

[3] The electrochemical sensor as described in [1] or [2], wherein a spare reference electrode is provide for use in place of the reference electrode when the means for examining the reference electrode detects an abnormal electric potential of the reference electrode.

[4] The electrochemical sensor as described in [1] to [3], wherein an informing measures is provided to inform the time of replacing the reference electrode when the abnormal electric potential is detected by the examining measures of the reference electrode.

[5] The electrochemical sensor as described in [1] to [4], wherein a switching measures of the reference electrode is provided by which the spare reference electrode is used in place of the reference electrode when the abnormal electric potential is detected by the means for examining the reference electrode.

[6] The electrochemical sensor as described in [1] to [5], wherein an immobilized enzyme layer is formed at least on the working electrode.

[7] The electrochemical sensor as described in [6], wherein a diffusion-limiting layer containing fluoroalcohol ester of polycarboxylic acid which is formed so as to cover at least the working electrode and the reference electrode is provided on the immobilized enzyme layer.

[8] An electrochemical sensor having a working electrode, a counter electrode and a reference electrode, wherein a spare electrode is provided for use in palace of the reference electrode when a use of the reference electrode is stopped.

[9] The electrochemical sensor as described in [8], wherein
a means for switching the reference electrode is provided by which the spare reference electrode is used in place of the reference electrode when the use of the reference electrode is stopped.

[10] The electrochemical sensor as described in [8] or [9], wherein an immobilized enzyme layer is formed at least on the working electrode.

[11] The electrochemical sensor as descried in [10], wherein
a diffusion-limiting layer containing a fluoroalcohol ester of polycarboxylic acid, which is formed so as to cover at least the working electrode and the reference electrode, is provided on the immobilized enzyme layer.

An electrochemical sensor having a means for examining a reference electrode as described above can detect immediately the situation wherein the reference electrode indicates an abnormal electric potential and does not function normally. According to a prior art, the abnormality of the sensor was confirmed by a calibration, that is, a method of detecting an abnormality in the sensor was adopted as a whole sensor system.

According to this method, however, it was difficult to confirm a malfunction of the reference electrode itself. Especially, when a natural electric potential of the reference electrode is getting out of a normal value although the reference electrode is not damaged, according to the prior art a measurement is performed assuming that the reference electrode is functioning normally without detecting the occurrence of abnormality and the measurement is, therefore, performed sometimes without noticing the abnormality.

On the other hand, the electrochemical sensor having the means for examining of the reference electrode can detect a small change in the electric potential of the reference electrode and can tell the time of replacement of the reference electrode exactly and, therefore, it is possible to increase reliability on a measured value.

Various kinds of means can be adopted for examining a reference electrode and a preferable structure consists of having an examining electrode as a standard used for measuring an electric potential of the reference electrode and a measuring apparatus used for measuring a potential difference between the examining electrode and the reference electrode. There is no restriction to a material and a structure of the examining electrode and the same structure as the reference electrode, for example, may be adopted. A voltmeter, for example, may be used for the measuring apparatus.

An electrochemical sensor having a spare reference electrode as described above can reduce a running cost and furthermore conduct a continuous measurement for a long time. According to a prior art, when a reference electrode is damaged, a whole substrate on which a group of electrodes is formed has to be replaced resulting in a hindrance to a continuous measurement and an increase in the running cost. On the other hand, according to the electrochemical sensor as described above, when a damage of the reference electrode is detected, the damaged reference electrode can be switched to the spare reference electrode without replacement of the whole substrate and a measurement with a high accuracy can be continued, which results in reducing the running cost.

A spare reference electrode is used in place of a reference electrode when the reference electrode does not function normally. It is, therefore, preferable to lengthen a life of the spare electrode so that the spare electrode does not damage before the reference electrode malfunctions. However, since the same material is often used for both the reference electrode and the spare electrode for reasons of processing, it is sometimes difficult to increase the life of the spare electrode by differentiating the material to be used.

The spare reference electrode is, therefore, preferably not connected to the same power source to which a working electrode, a counter electrode and the reference electrode are connected and a voltage is also preferably not kept applied to the spare reference electrode. A photoresist may be coated on the spare electrode to lengthen the life of the spare reference electrode.

Since the sensor of this invention has an examining electrode, it is possible to detect an abnormality in the reference electrode immediately after its occurrence and increase the reliability of measured value by removing the abnormality quickly. If the sensor has a spare reference electrode, it possible to conduct a continuous measurement for a long time and to reduce the running cost.

DESCRIPTION OF THE PREFERRED EMBODIMENT

Figure 1:
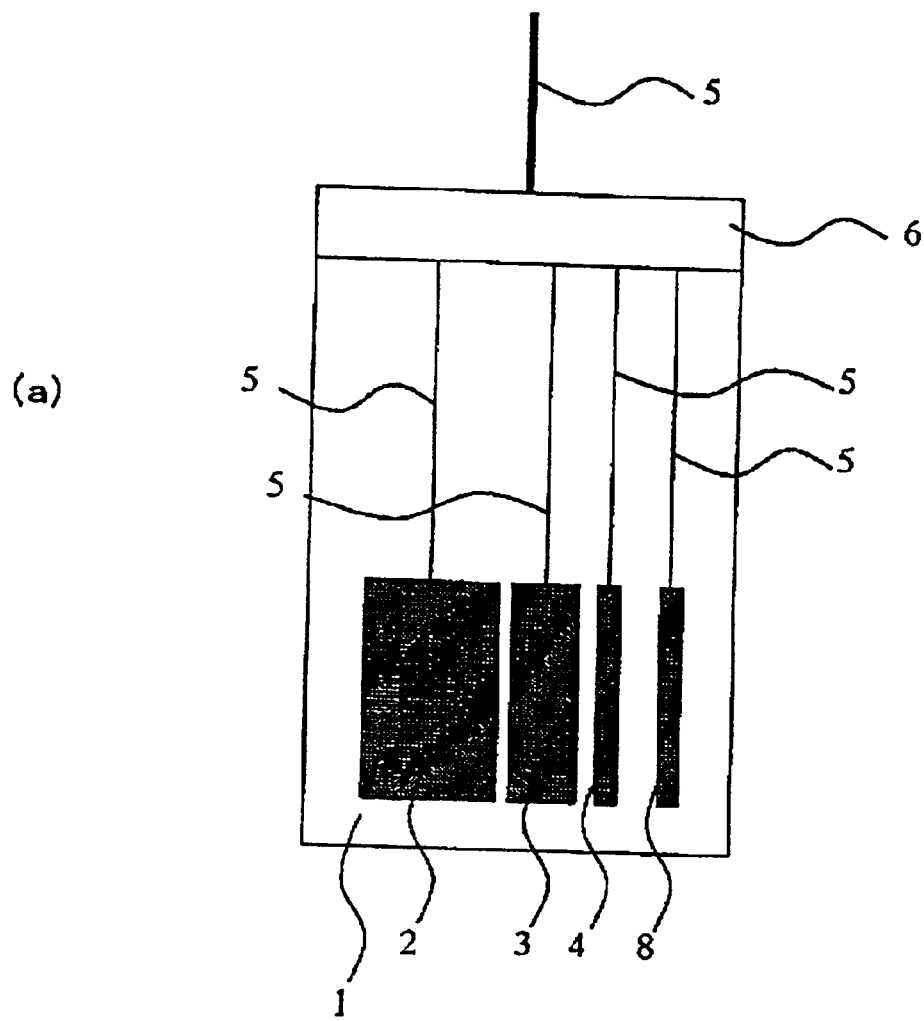
FIGS. 1(a)–1(b) shows a structure of a sensor relating to this invention.
Figure 1:
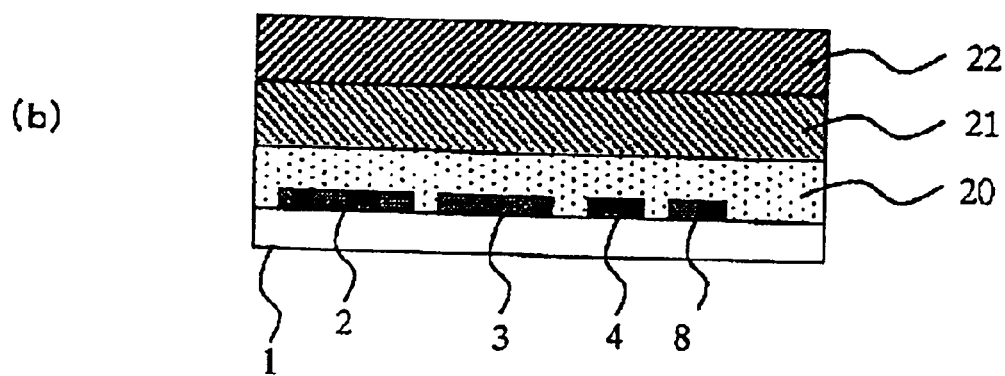

There is no restriction on the number of a working electrode and a counter electrode in this invention. When measuring plural components by a single sensor, installation of plural working electrodes and counter electrodes may be effective. On the other hand, regarding to a reference electrode, a preferable structure consists of the reference electrode used for measurement and a spare reference electrode.

Plural examining electrodes may be used although one examining electrode may be used usually in this invention. The examining electrode is used for examining an electric potential and it may be possible to adopt a method of a continuous examining or of examining before measurement. The examining electrode may be formed in common use with the spare reference electrode.

A spare reference electrode is used in place of a reference electrode. A switching the spare electrode to the reference electrode may be executed based on the time of measurement, the number of times of measurement, an occurrence of an abnormality such as decrease in an electric potential. During the reference electrode is in use, the spare reference electrode is not used. Changing an electric circuit automatically by a program installed in the sensor may practice the switching the reference electrode to the examining electrode. Manual switching from reference electrode to the examining electrode is also available, by receiving information of replacement from means for informing. This switch is installed in the sensor. This switch is installed in the sensor.

When a method of switching on detection of an abnormal electric potential by a means for examining a reference electrode is adopted, decision criteria of an abnormality are set appropriately according to a purpose and a use of measurement, for example, when the electric potential fluctuates more than 10 mV it is judged as abnormal.

In this invention a preferable structure consists of having both an examining electrode and a spare reference electrode on the same substrate. According to the structure, abnormality on the reference electrode is detected immediately and accurately and a highly accurate measurement may be performed continuously by switching the reference electrode to the spare reference electrode. In this case, since a replacement of a whole substrate on which a group of electrodes is formed is not necessary, a running cost may be reduced greatly.

In this invention a working electrode, a counter electrode, a reference electrode and a spare reference electrode are preferably formed on the same substrate and in this way a sensor is easily miniaturized as well as a manufacturing process becomes simple.

A preferable structure of a sensor in this invention may be, for example, a sensor having a working electrode on which at least an immobilized enzyme layer is formed. The sensor of this structure is based on a measuring method combining an enzyme reaction and an electrochemical reaction and the measuring method may adopt, for example, measuring an amount of a generated substance to which a chemical substance present in a solution has been converted by the catalytic function of the enzyme. A glucose biosensor, for example, oxidizes glucose by a glucose oxidase (GOX) to generate gluconic lactone and hydrogen peroxide and a determination of the glucose concentration is made by measurement of the generated hydrogen peroxide. It is possible to adopt another method in which the determination of the glucose concentration is made by measuring a decrease in oxygen-reduction current associated with a decrease in oxygen in the neighborhood of the enzyme layer.

In the case of a sensor having an immobilized enzyme layer as described above, a preferable structure consists of providing a diffusion-limiting layer containing a fluoroalcohol ester of polycarboxylic acid which is formed so as to cover at least a working electrode, a counter electrode, a reference electrode and an examining electrode on the immobilized enzyme layer. In this way, an excessive diffusion of a chemical substance to be measured is limited and a possible range of measurement may be extended to a high concentration and a high accuracy in the measurement of a low concentration area is made possible. Furthermore, a stability of measurement may be raised by limiting diffusion of pollutants and interfering substances. Pollutants are substances that reduce the accuracy of measurement by depositing on the electrodes and are, for example, protein or urea compounds when a body fluid is used as a sample to be measured. Interfering substances are substances, which reduce the accuracy of measurement by interfering with an electrode reaction. In a sensor, which measures hydrogen peroxide generated from glucose, the interfering substances are, for example, ascorbic acid, uric acid and acetaminophen.

A senor having an immobilized enzyme layer demonstrates the effects of this invention more remarkably by making the life of a reference electrode longer due to reducing the effects of interfering substances. When the life of the reference electrode is short, it is a general way of usage that when a predetermined period has passed, the reference electrode is replaced immediately with a new electrode.

On the other hand, when a sensor having a long life of the reference electrode is used, it is possible to continue to use the sensor until there occurs an abnormality in one of the electrodes including the reference electrode without determining the replacement time beforehand. However, it is necessary to know the time of replacement of an electrode exactly in order for such a way of usage to be possible.

As described above, the reference electrode may affect measuring value by the fluctuation of the electric potential even if it is not damaged and it is, therefore, important to find the time of replacement accurately by detecting such situation. According to this invention, since detecting a fine change of electric potential of the reference electrode is possible, it is possible to know the time of replacement exactly and the advantage of the long life by having the diffusion-limiting layer as described above can be fully utilized.

In this invention, a preferable structure consists of having means for informing to tell the time of replacing a reference electrode when an abnormal electric potential is detected by a means for examining the reference electrode. By this way it is possible to know the time of replacing the reference electrode exactly. As the means for informing, in addition to a method of indicating the time of replacing the reference electrode on a display connected to the sensor, transmitting methods by sound, light, vibration, color, a figure and heat may also be adopted.

Preferable embodiments are explained referring to the drawings in the followings:

(The First Embodiment)

Figure 3:
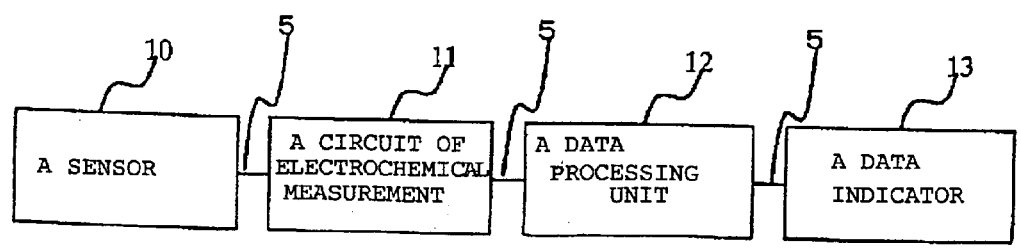
FIG. 3 shows a rough structure of a measuring apparatus including a sensor relating to this invention.

A structure of a sensor relating to the embodiment is shown in FIGS. 1(a)–1(b) and a whole structure of a measuring apparatus including the sensor is shown in FIG. 3.

The sensor of the embodiment shown in FIGS. 1(a)–1(b) is a biosensor wherein a substance to be measured is converted to another substance by an enzyme reaction and the concentration of the converted substance is measured electrochemically. A working electrode 2, a counter electrode 3 and a reference electrode 4 is formed on an insulating substrate 1. An examining electrode 8 that measures and examines an electric potential of the reference electrode 4 is formed on the substrate. On these electrode are formed a combining layer 20 (membrane thickness: about 10–50 nm), an immobilized enzyme layer 21 (membrane thickness: about 200–1000 nm) and a diffusion-limiting layer 22(membrane thickness: about 20–200 nm) in this order. The wiring 5 may be an electric wire which can connects them. The cover 6 is placed so as to protect them.

Materials used for the insulating substrate 1 consist mainly of high insulating materials such as, for example, ceramics, glass, quartz and plastics. The materials having excellent properties of water-resistance, heat-resistance, chemical-resistance and close adherence to an electrode are preferable.

Materials which consist mainly of platinum, gold, silver and carbon may be used for the working electrode 2 and the counter electrode 3, and among them platinum is preferably used which has excellent properties of chemical-resistance and of detecting hydrogen peroxide.

The working electrode 2 and the counter electrode 3 on the insulating substrate 1 may be formed by the methods of spattering, ion plating, vacuum deposition, chemical vapor deposition and electrolysis, and among them the method of spattering is preferable because close adherence of the electrodes to the insulating substrate 1 is excellent and a platinum layer is easily formed and a flat and smooth surface of the platinum layer is obtained. In order to improve the close adherence of the working electrode 2 and the counter electrode 3 to the insulating substrate 1, a layer of titanium or chromium may be provided between them.

The reference electrode 4 and the examining electrode 8 have the same structure in this invention. These electrodes may consist of various materials and a silver/silver chloride electrode (an electrode containing a structure of silver chloride layered on silver) is preferable which is made by a simple and easy process and has a stable characteristic.

A preferable structure of the silver/silver chloride electrode is a multi-layer of titanium, silver and silver chloride layered in this order or a multilayer of titanium, platinum, silver and silver chloride layered in this order due to the excellent sensitivity and strength. The reference electrode 4 and the examining electrode 8 may be formed by the various methods such as spattering, ion plating, vacuum deposition, chemical vapor deposition and electrolysis.

For example, when a silver/silver chloride electrode is to be made, a silver membrane is formed first and then the membrane is dipped in an aqueous solution containing a chlorine compound having a larger ionization tendency than silver, for example, an aqueous solution of iron chloride. The silver membrane may be formed by the methods of silver mirror reaction, spattering, ion plating, vacuum deposition and chemical vapor deposition, and among them the spattering method is preferable by which a mass production is easy and a good flat and smooth surface is obtained.

To prepare a solution in which a substrate with a silver membrane formed is dipped, metal chlorides having lower ionization tendency or oxidation-reduction potential than silver, for example, iron chloride (III), copper chloride (I) and (II), iron chloride (II), lead chloride, tin chloride, nickel chloride, chromium chloride, zinc chloride and manganese chloride may be used and among them iron chloride (III) is preferable because it is a compound of low cost and low poison. When iron chloride (III) solution is used, a concentration of 1 mM or more is sufficient and 50 mM or a little more is preferable.

The combining layer 20 formed on the working electrode 2 improves the adherence (combining force) among the immobilized enzyme layer 21 on the combining layer 20, the insulating substrate 1 and the electrodes including the working electrode 2. Furthermore the combining layer 20 improves wettability of the surface of the insulating substrate 1 and has the effect of improving uniformity of membrane thickness when forming the immobilized enzyme layer 21 in which enzyme is immobilized. Furthermore the combining layer 20 has selective diffusion capability to ascorbic acid, uric acid and acetaminophen that interfere the reaction of hydrogen peroxide generation on the working electrode 2. The combining layer 20 consists of mainly silane coupling agents. The silane coupling agents are, for example, aminosilane, vinylsilane and epoxysilane and in the light of the adherence and the selective diffusion capability to γ-aminopropyltriethoxysilane, a kind of aminosilane, is preferable. The combining layer 20 may be formed by spin-coating of a solution of a silane-coupling agent wherein a preferable concentration of the silane-coupling agent is about 1 v/v % (volume/volume %), because the selective diffusion capability is improved remarkably.

The immobilized enzyme layer 21 is formed by immobilizing an enzyme having a catalytic function as a mother material of an organic polymer. The immobilized enzyme layer 21 is formed by a spin-coating method by dropping a solution containing, for example, various enzymes, a protein cross-linking agent such as glutaraldehyde and albumin on the combining layer 20. Albumin protects the enzymes from the reaction of the cross-linking agent and is a basic material of the protein. The enzymes that produce hydrogen peroxide as a product of the catalytic reaction or consume oxygen are, for example, lactic acid oxidase, glucose oxidase, uric acid oxidase, galactose oxidase, lactose oxidase, sucrose oxidase, ethanol oxidase, methanol oxidase, starch oxidase, amino acid oxidase, monoamine oxidase, cholesterol oxidase, choline oxidase and pyruvic acid oxidase.

More than two kinds of enzyme, for example, creatininase, creatinase and sarcosine oxidase may be used simultaneously where the detection of creatinine is possible. An enzyme and a coenzyme, for example, 3-hydroxybutyric acid anhydrase and nicotinamide adenine dinucleotide (NAD+) may be used simultaneously where the detection of 3-hydroxybutyric acids is possible. Furthermore an enzyme and an electron mediator may be used simultaneously where an electric current obtained by the oxidation of the electron mediator reduced by the enzyme is measured; for example, glucose oxidase and potassium ferricyanide are used simultaneously and the detection of glucose is possible by measuring the electric current obtained.

As mentioned above, there is no limitation to the immobilized enzyme layer 21 as for as it consists of a structure containing at least one kind of enzyme and having a function by which a substance to be measured is converted to an electrode-sensitive substance (for example, hydrogen oxide). There is no limitation to a method of forming the immobilized enzyme layer 21 as far as it can form a uniform membrane thickness and a screen printing method may be used other than a spin-coating method.

The diffusion-limiting layer 22 is formed on the immobilized enzyme layer 21 so as to cover the working electrode 2, the counter electrode 3, the reference electrode 4 and the examining electrode 8. The diffusion-limiting layer 22 preferably contains fluoroalcohol ester of polycarboxylic acid. The fluoroalcohol ester of polycarboxylic acid is a compound in which a part or all of the polycarboxylic acid is esterified by fluoroalcohol. The fluoroalcohol is the alcohol wherein all of or at least one of the hydrogen in the alcohol is substituted by fluorine.

As the fluoroalcohol ester of polycarboxylic acid, for example, polymethacrylic acid 1H, 1H-perfluorooctyl or polyacrylic acid 1H, 1H, 2H, 2H-perfluorodecyl may be used. The molecular weight of the polymer constituting the diffusion-limiting layer is preferably 1000 to 50000 and more preferably 3000–30000. If the molecular weight is too large, a preparation of solution is difficult and the lamination of the diffusion-limiting layer becomes hard. If the molecular weight is too small, sufficient diffusion-limiting capability is not obtained. The molecular weight as used herein means a number average molecular weight and is measured by GPC (Gel Permeation Chromatography).

The diffusion-limiting layer 22 may be formed by a spin-coating method wherein a solution of fluoroalcohol ester of methacrylic resin diluted with perfluorocarbon solvent such as perfluorohexane is dropped on the immobilized enzyme layer 21 wherein an enzyme having a catalytic function is immobilized. The concentration of fluoroalcohol ester of methacrylic resin in the solution is preferably 0.1–5 wt % and more preferably about 0.3 wt % depending on the substance to be measured since Excellent diffusion-limiting capability is realized by applying the range of the concentration. There is no limitation to the method of forming the diffusion-limiting layer 22 as far as the layer with a uniform thickness is obtained and a method of spray coating or a dip-coating other than the spin-coating method may be used.

When a sensor of the embodiment of this invention is used as a glucose sensor, the diffusion-limiting layer 22 of the outermost layer limits the diffusion rate of glucose and the diffusing glucose reacts with oxygen catalytically by the organic polymer membrane having glucose oxidase to produce hydrogen peroxide and gluconic lactone. It is possible to know the concentration of the glucose by measuring the electric current observed when the hydrogen peroxide reaches the working electrode 2.

An outline of a whole structure of the measuring apparatus as described above will be explained referring to FIG. 3.

The measuring apparatus consists of a sensor 10, a circuit of electrochemical measurement 11, a data processing unit 12 and a data indicator 13 and all of them are connected by a wiring 5. The sensor 10 has a structure as explained according to FIGS. 1(a)–1(b). Since the sensor 10 is expendables, an exchangeable type by which replacement is easily performed is preferable. As the circuit of electrochemical measurement 11 a potentiostat is used in the embodiment of this invention, and there is no limitation to the circuit as far as the circuit can apply a constant electric potential to the sensor 10 and measure an electric current.

The data processing unit 12 has a function of calibrating electrodes, measurements, and storing measured data. For example, it may have a structure including means for informing the replacement time of each electrode used in the sensor and of the flow of abnormal electric current in the sensor. As the data processing unit 12, a personal computer is used in the embodiment of this invention, and there is no limitation to the unit as far as it has an arithmetic logic unit such as a microprocessor that can process a signal from the circuit of electrochemical measurement 11. The signal that has been processed in the data processing unit 12 is converted to a measured value and is indicated as the measured value on the data indicator 13.

The means for indicating the time of replacement of electrode may, for example, be provided for the reference electrode. Judgment of the time of replacement may be decided based on a measurement time, a number of measuring times, a decrease in the electric potential of the electrode.

The data indicator 13 uses a display of personal computer and there is no limitation to the indicator as far as it has a function of indicating the data processed by the data processing unit 12. The data is displayed in the embodiment of this invention and other forms of a means for indicating such as sound, light, vibration, color, a figure and heat may be used to transmit the contents of the data. The wiring 5 may be an electric wire which can connects them.

The sensor of the embodiment of this invention has a voltmeter between the reference electrode 4 and the examining electrode 8, and an electric potential of the reference electrode 4 can be examined by the examining electrode 8. As described above, the reference electrode 4 may sometimes affect a measured value by the fluctuation of the electric potential even if the electrode is not damaged. Since the sensor of the embodiment of this invention has the reference electrode 8, it can detect a fine change of the electric potential of the reference electrode 4, find the replacement time accurately and increase the reliability of measured values.

Furthermore, in the case of adopting the configuration having the diffusion-limiting layer 22 of a specified structure as in the embodiment of this invention, due to the limitation of diffusion pollutants and interfering substances, the life of the reference electrode becomes longer as compared with the conventional sensor and, therefore, as described above it is particularly important to detect the change of the electric potential of the reference electrode exactly. In this regard, since the sensor of the embodiment of this invention can detect accurately a change of the electric potential of the reference electrode 4 by the examining electrode 8, an advantage of the longer life can be fully utilized by providing for the diffusion-limiting layer 22.

(The Second Embodiment)

Figure 2:
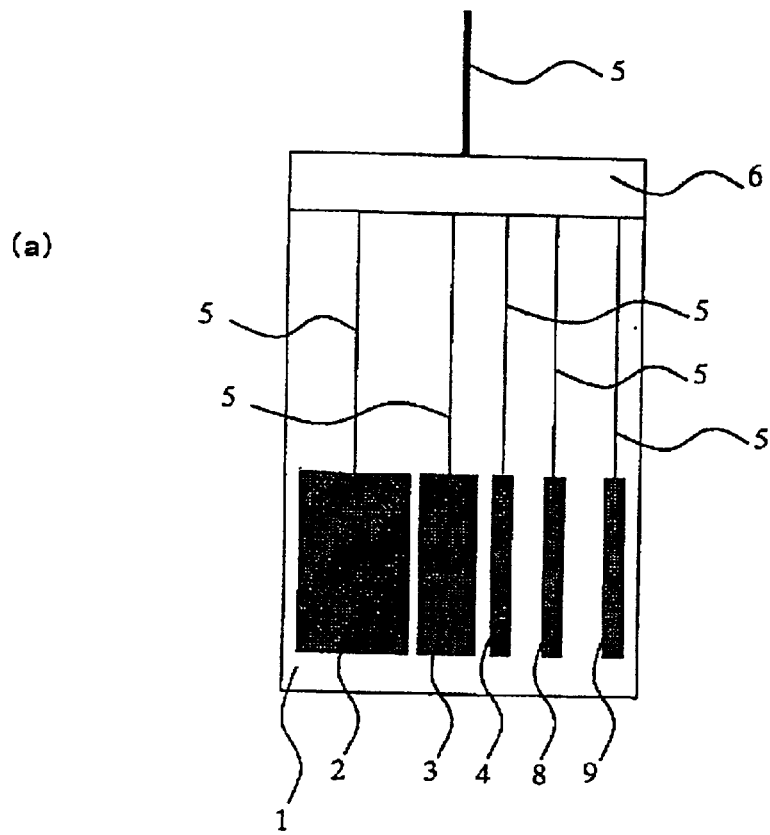
FIGS. 2(a)–2(b) shows a structure of a sensor relating to this invention.
Figure 2:
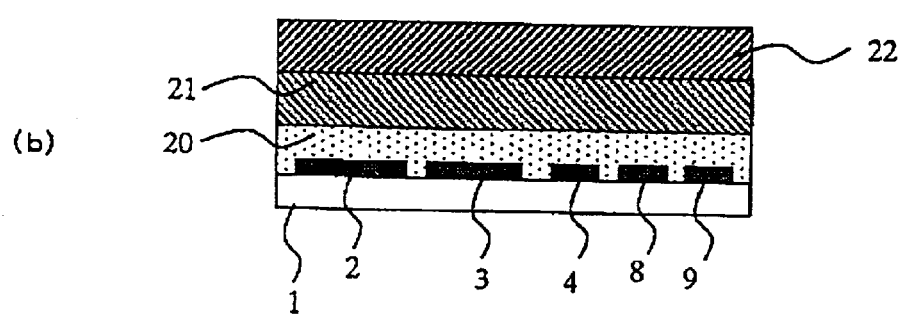

A structure of a sensor relating to the embodiment is shown in FIGS. 2(a)–2(b). A basic structure of the sensor is nearly the same except for providing a spare reference electrode 9. The spare reference electrode 9 is used in place of the reference electrode 4 when an abnormal electric potential is detected in the reference electrode 4.

Figure 4:
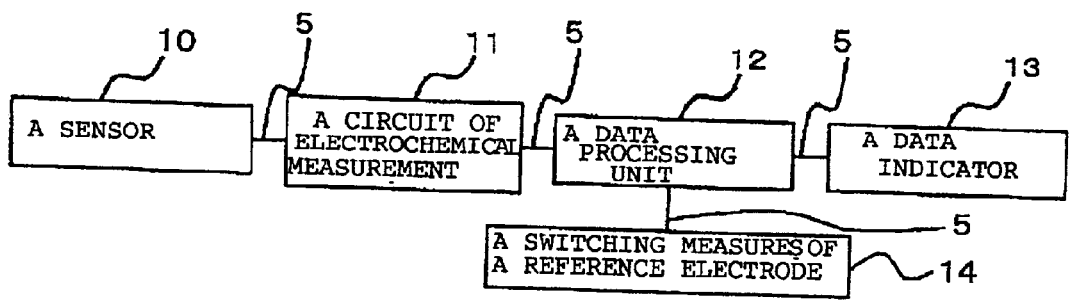
FIG. 4 shows a rough structure of a measuring apparatus including a sensor relating to this invention.

A whole structure of a measuring apparatus including the sensor is shown in FIG. 4. The measuring apparatus consists of a sensor 10, an electrochemical measuring circuit 11, a data processing unit 12 and a data indicator 13 and all of them are connected by a wiring 5. A means for switching 14 is provided for the data processing unit 12 that is different from the apparatus shown in FIG. 3.

Figure 14:
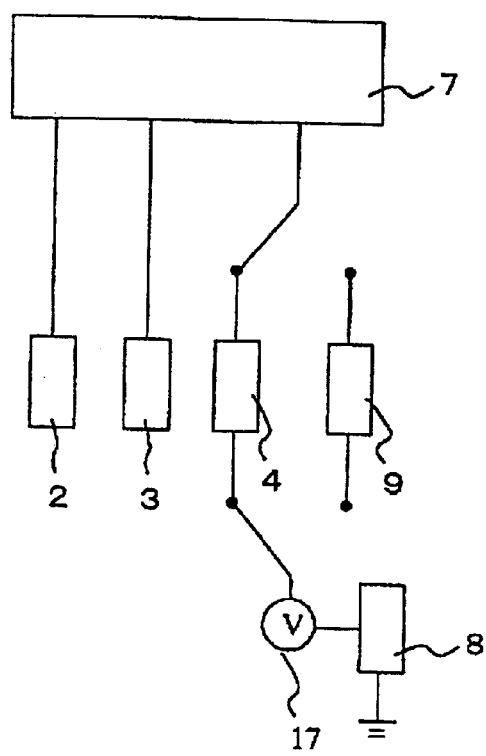
FIGS. 14(a)–14(b) shows a structure of a sensor relating to this invention.
Figure 14:
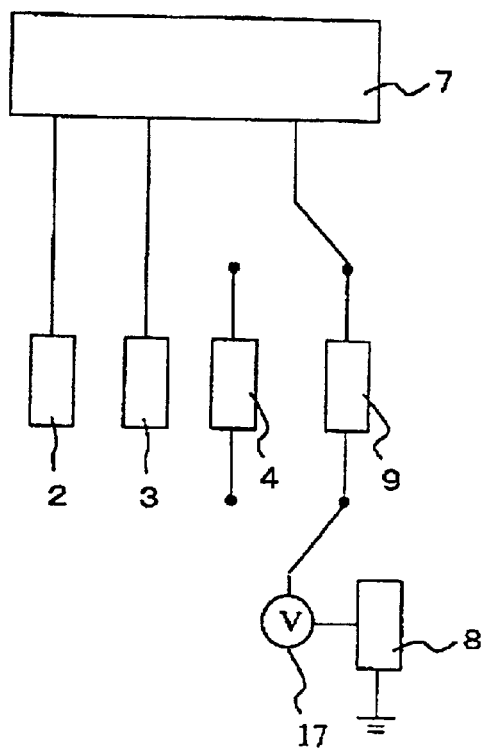
Figure 15:
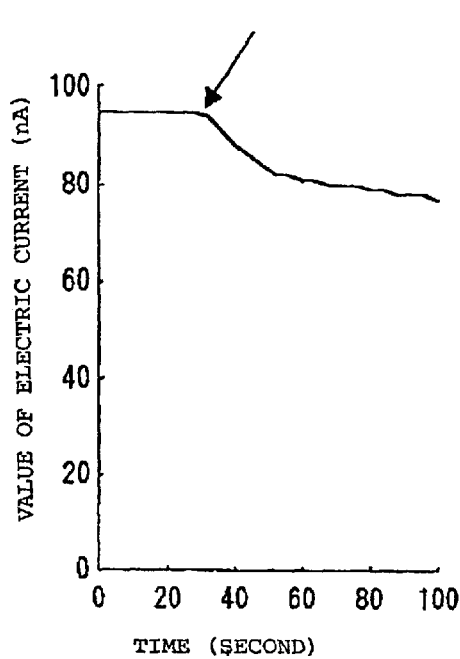
FIGS. 15(a)–15(b) shows the effects of an interfering substance on an output of a sensor and an electric potential of a reference electrode.
Figure 15:
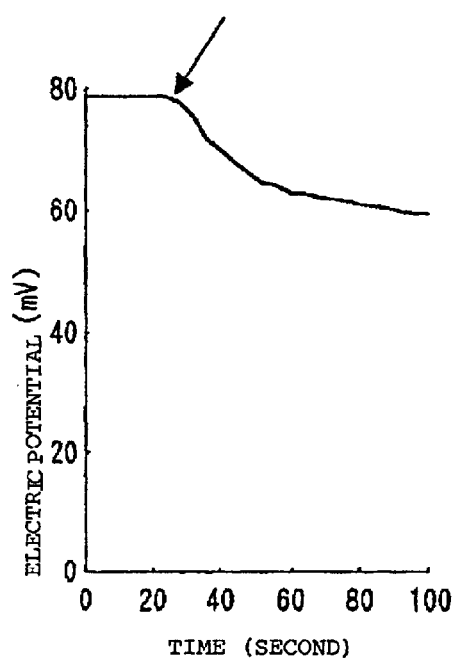

The measuring apparatus shown in this embodiment is in the state of FIG. 14(a) at the beginning. The working electrode 2, the counter electrode 3 and the reference electrode 4 are connected to a potentiostat 7 so that electric potentials of the working electrode 2 and the counter electrode 3 are controlled to specified values.

The examining electrode 8 is grounded and a voltmeter 17 is provided between the reference electrode 4 and the examining electrode 8 so that the examining electrode 8 can examine the electric potential of the reference electrode 4. The examining electrode 8 is connected to a means for switching the reference electrode which is not shown in FIGS. 14(a)–14(b) and the means for switching the reference electrode performs the switching so that the spare electrode can be used when an abnormal electric potential is detected in the reference electrode 4.

FIG. 14(b) shows the state after the reference electrode has been switched to the spare reference electrode 9. As a means for switching 14 of the reference electrode, a switching program of the reference electrode stored in a built-in memory of the measuring apparatus is used in this embodiment.

According to a sensor of this embodiment, since the sensor is provided with the spare reference electrode 9 and the means for switching 14 of the reference electrode, it is possible to detect an abnormality in the reference electrode 4 immediately and increase the reliability of measured values by removing the abnormality quickly. Furthermore, a long continuous measurement is possible and a running cost can be reduced because the frequency of replacing the substrate on which electrodes are formed can be reduced.

EXAMPLE 1

A sensor shown in FIGS. 1(a)–1(b) was made and the performance of the sensor was evaluated. A procedure of making the sensor is explained as follows:

A working electrode, a counter electrode, a reference electrode and an examining electrode were formed on a 10 mm×6 mm quartz substrate. The working electrode (area: 7 mm$^2$) and the counter electrode (area: 4 mm$^2$) are made of platinum. The reference electrode and the examining electrode have a multi-layer structure of silver/silver chloride; at first silver membranes were formed on the substrate by the spattering method and then the substrate was dipped in an aqueous solution of iron chloride to form the reference electrode and the examining electrode.

Next, after a combining layer was formed by spin-coating a 1 v/v % solution of -aminopropyltriethoxysilane, an immobilized enzyme layer was formed by spin-coating a 22.5 w/v % albumin solution containing glucose oxidase and 1 v/v % glutaraldehyde. Then, after spin-coating a 0.3 wt % solution of fluoroalcohol ester of methacrylic resin prepared by perfluorohexane on the immobilized enzyme layer, a diffusion-limiting layer was formed by drying the layer. The spin-coating was performed at the condition of 3000 rpm and 30 sec. The fluoroalcohol ester of methacrylic resin used was Fluorad® FC-722; a product of SUMITOMO 3M Limited. Fluorad® FC-722 is a polymethacrylic acid 1H, 1H-perfluorooctyl and has an average molecular weight (Mn) of about 7000 (GPC value). The diluting solvent used, perfluorohexane, was Fluorad® FC-726, a product of SUMITOMO 3M Limited. The thickness of the diffusion-limiting layer was about 50 nm. Thus the sensor was made according to the procedure as described above.

Then, the sensor was connected to a circuit of electrochemical measurement, a data processing unit and a data indicator with a wiring. A potentiostat, HOKUTODENKOPOTENTIOSTAT/GALVANOSTATHA150G, a product of Hokutodenko Co., was used as the circuit of electrochemical measurement. A personal computer, PC-9821RaII23, a product of NEC Co. was used as the data processing unit. A display, PC-KP531, a product of NEC Co. was used as the data indicator.

Figure 5:
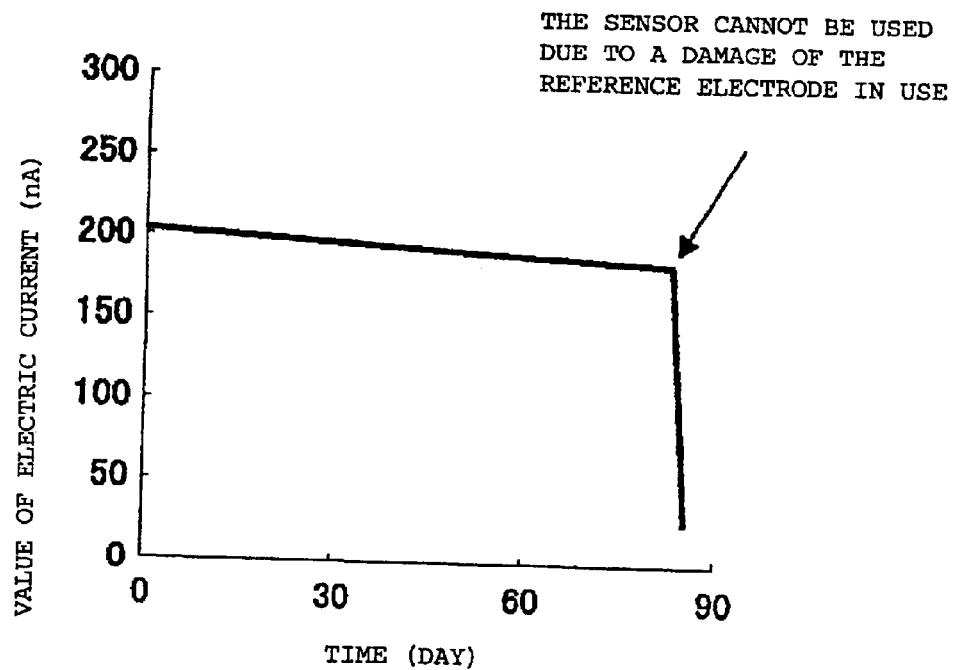
FIG. 5 shows an output change vs. time of a sensor evaluated in the example.
Figure 6:
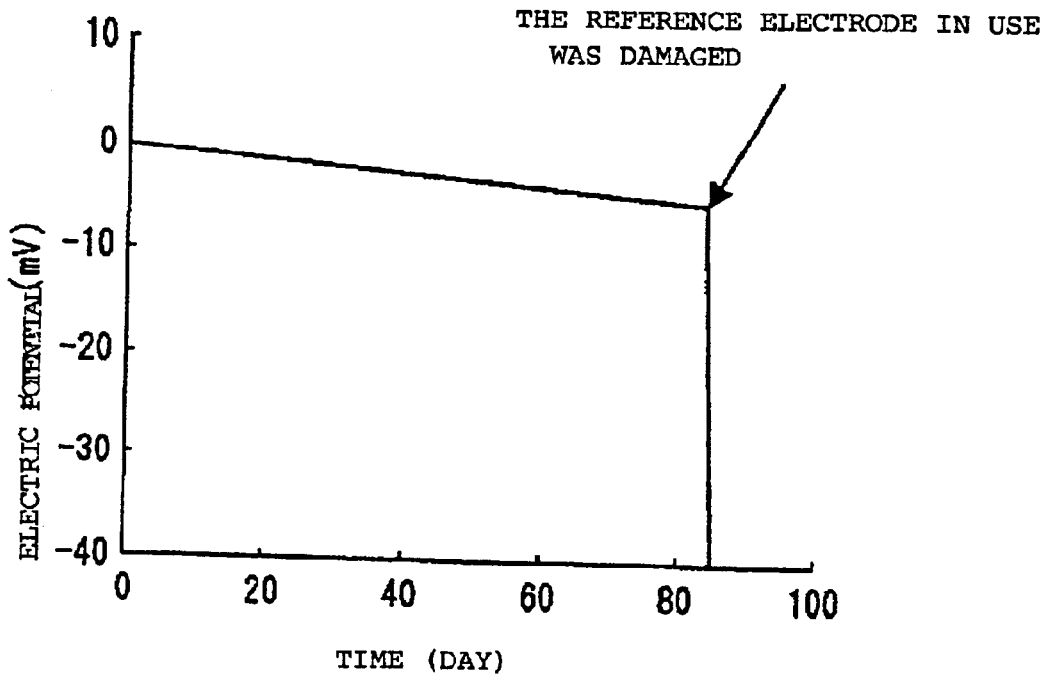
FIG. 6 shows an output change vs. time of an electric potential of a reference electrode evaluated in the example.

Then, the sensor was stored dipped in a buffer solution of pH7 TES (N-tris (hydroxymethyl)-methyl-2-aminoethanesulfonic acid) containing 150 mM of sodium chloride and measurements of 200 mg/dl glucose were performed once or several times a day. FIG. 5 shows the results of the electric current measured, indicating the output from the sensor corresponding to the glucose. FIG. 6 shows the result of the measurements of the natural electric potential of the reference electrode functioning as a standard electrode. As a result of the measurements, it was confirmed that a normal measurement became impossible due to a reduction in the natural electric potential associated with a damage that occurred in the reference electrode on the 82$^{nd}$ day.

According to the example, since an examining electrode had been provided, the abnormality of the sensor was confirmed to be due to the damage of the reference electrode.

EXAMPLE 2

In this example a sensor shown in FIGS. 2(a)–2(b) was made and the performance of the sensor was evaluated. The procedure of making the sensor is explained as follows:

A working electrode, a counter electrode, a reference electrode, an examining electrode and a spare reference electrode were formed on a 10 mm×6 mm quartz substrate. The working electrode (area: 7 mm$^2$) and the counter electrode (area: 4 mm$^2$) are made of platinum. The reference electrode and the examining electrode have a multi-layer structure of silver/silver chloride; at first a silver membranes were formed on the substrate by the spattering method and then the substrate was dipped in an aqueous solution of iron chloride to form the reference electrode and the examining electrode.

Next, as example 1, after a combining layer was formed by spin-coating a 1 v/v % solution of -aminopropyltriethoxysilane, an immobilized enzyme layer was formed by spin-coating a 22.5 w/v % albumin solution containing a glucose oxidase and a 1 v/v % glutaraldehyde and further a diffusion-limiting layer was formed by Fluorad® FC-722 (polymethacrylic acid 1H, 1H-perfluorooctyl).

A sensor without having a spare reference electrode was made as a comparative example.

Then, the sensor was connected to a circuit of electrochemical measurement, a data processing unit and a data indicator with a wiring.

A potentiostat, HOKUTODENKOPOTENTIOSTAT/GALVANOSTRATHA 150G, a product of Hokutodenko Co., was used as the circuit of electrochemical measurement. A personal computer, PC-9821RaII23, a product of NEC Co. was used as the data processing unit. A display, PC-KP531, a product of NEC Co. was used as the data indicator. In the data processing unit a program is written which instructs to switch to the spare reference electrode when an electric potential of the reference electrode in use changes more than 10 mV, i.e., an abnormality occurs in the reference electrode.

Then, these sensors were stored dipped in a buffer solution of pH 7 TES (N-tris (hydroxymethyl)-methyl-2-aminoethanesulfonic acid) containing 150 mM of sodium chloride and measurements of 200 mg/dl glucose was performed once or several times a day.

Figure 7:
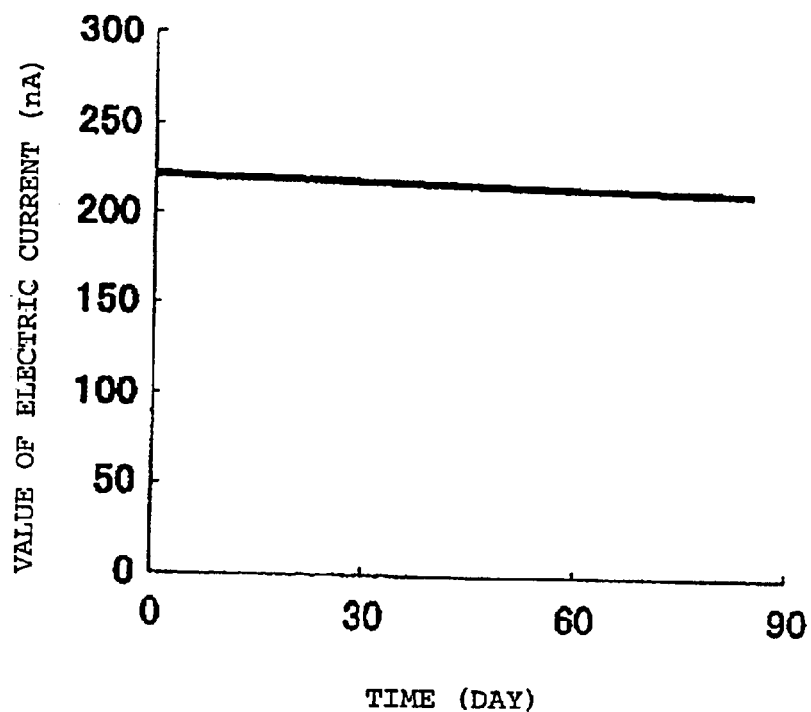
FIG. 7 shows an output change vs. time of a sensor evaluated in the example.
Figure 8:
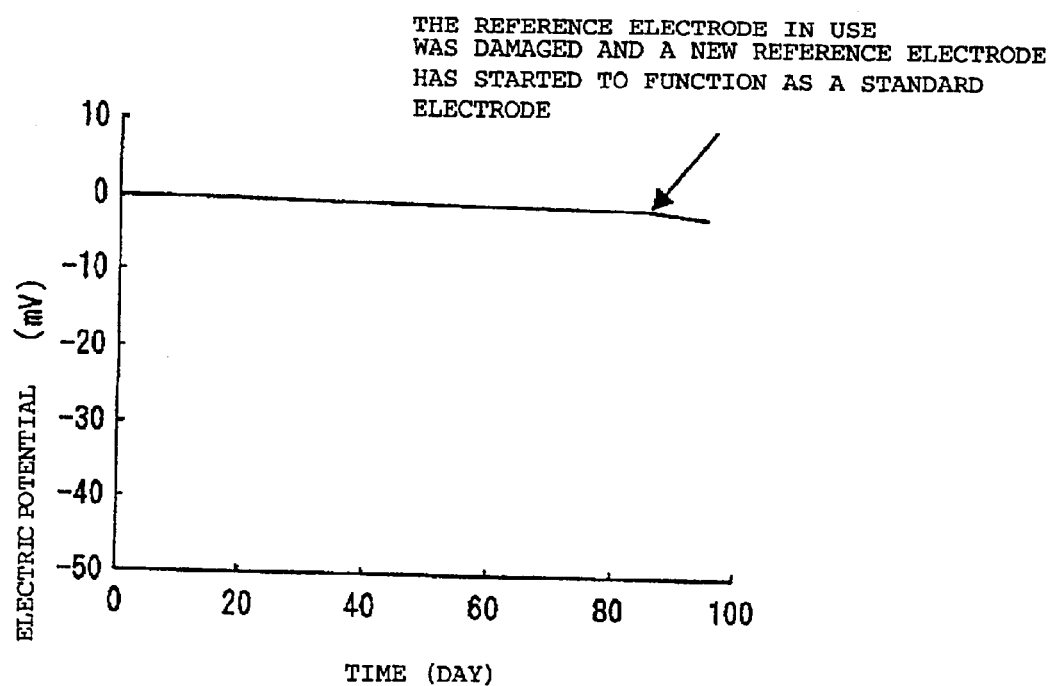
FIG. 8 shows an output change vs. time of an electric potential of a reference electrode evaluated in the example.

In FIG. 7 and FIG. 8 are shown the results of evaluation relating to the example of the sensor having an examining electrode and a reference electrode. FIG. 7 shows a sensor output (electric current) relating to glucose and FIG. 8 shows a natural electric potential of the reference electrode. In this example, on the 82$^{nd}$ day of the measurements a reduction in the natural electric potential associated with a damage of the reference electrode occurs. Then, when the remaining spare reference electrode was started to be used, it was found that a normal natural electric potential was obtained and a normal measurement was restored.

On the other hand, in a sensor without having an examining electrode and a spare reference electrode, it was impossible to confirm whether a normal measurement was possible or not and to find the time of replacement of the reference electrode as described above.

EXAMPLE 3

Figure 9:
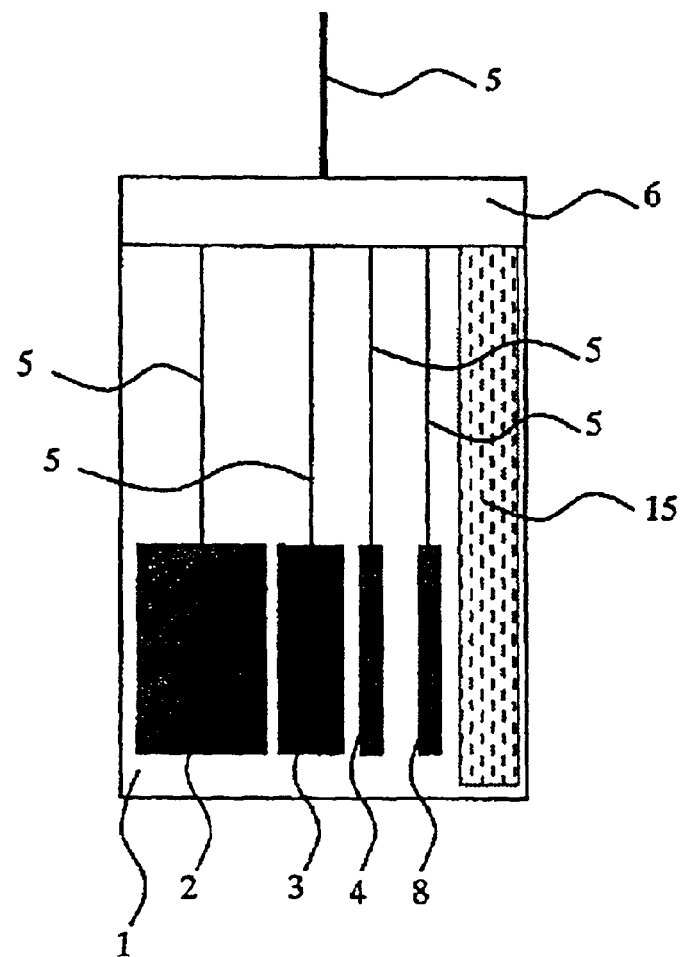
FIGS. 9(a)–9(c) shows a structure of a sensor relating to this invention.
Figure 9:
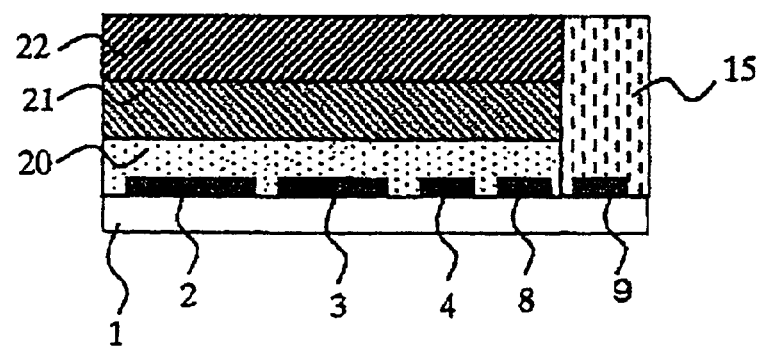

In this example, a sensor shown in FIGS. 9(a)–9(b) was made and a performance of the sensor was evaluated. A spare reference electrode 9 of this sensor is coated with a photoresist 15. The procedure of making the sensor is explained as follows:

A working electrode, a counter electrode, a reference electrode, an examining electrode and a spare reference electrode were formed on a 10 mm×6 mm quartz substrate. The working electrode (area: 7 mm$^2$) and the counter electrode (area: 4 mm$^2$) are made of platinum. The reference electrode, the examining electrode and the spare reference electrode have a multi-layer structure of silver/silver chloride; at first silver membranes were formed by a spattering method and then the substrate was dipped in an aqueous solution of iron chloride to form the reference electrode, the examining electrode and the spare reference electrode.

Then, a photoresist layer was formed on the surface of the spare reference electrode by a method of photolithography. As the photoresist OFPR800, a product of TOKYO OUKA KOUGYOU Co., LTD. was used.

Next, as described in Example 1, after a combining layer was formed by spin-coating a 1 v/v % solution of -aminopropyltriethoxysilane, a immobilized enzyme layer was formed by spin-coating a 22.5 w/v % albumin solution containing glucose oxidase and a 1 v/v % glutaraldehyde and further a diffusion-limiting layer were formed by Fluorad® FC-722 (polymethacrylic acid 1H, 1H-perfluorooctyl).

A sensor without having an examining electrode and a spare reference electrode was made as a comparative example.

Then, the sensor was connected to a circuit of electrochemical measurement, a data processing unit and a data indicator with a wiring.

A potentiostat, HOKUTODENKOPOTENTIOSTAT/GALVANOSTATHA 150G, a product of Hokutodenko Co., was used as the circuit of electrochemical measurement. A personal computer, PC-9821RaII23, a product of NEC Co. was used as the data processing unit. A display, PC-KP531, a product of NEC Co. was used as the data indicator. In the data processing unit a program is written which instructs to switch to the spare reference electrode when an electric potential of the reference electrode in use changes more than 10 mV, i.e., abnormality occurs in the reference electrode.

Then, the sensor was stored dipped in a buffer solution of pH7 TES (N-tris(hydroxymethyl)-methyl-2-aminoethanesulfonic acid) containing 150 mM of sodium chloride and measurements of 200 mg/dl glucose was performed once or several times a day.

Figure 10:
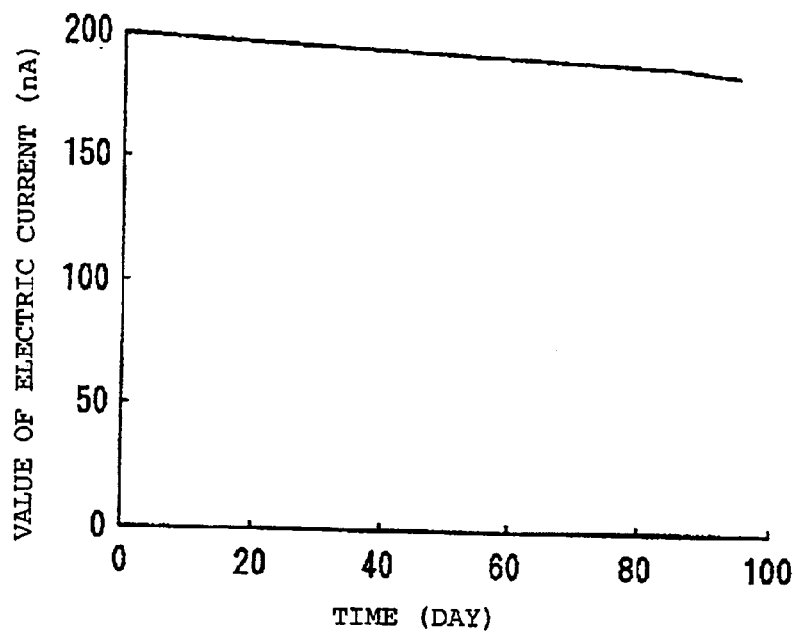
FIG. 10 shows an output change vs. time of a sensor evaluated in the example.
Figure 11:
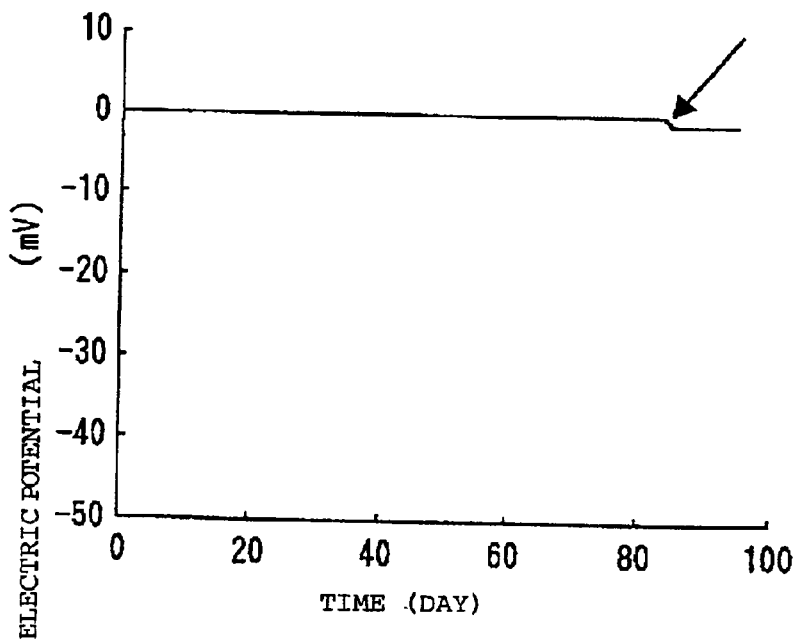
FIG. 11 shows an output change vs. time of an electric potential of a sensor evaluated in the example.

In FIG. 10 and FIG. 11 are shown the results of evaluation relating to the example of the sensor having an examining electrode and a reference electrode. FIG. 10 shows a sensor output (electric current) relating to glucose and FIG. 11 shows a natural electric potential of the reference electrode.

The results shown in FIG. 10 indicates a stable measurement of glucose by the sensor relating to this example for 95 days and a reduction in a natural electric potential (data is not shown in the figure) associated with a damage of the reference electrode occurred on the $82^{nd}$ day of the measurements. Then, the photoresist formed on the reference electrode was removed by dipping the sensor in an acetone solution. When the reference electrode was started to be used as a standard electrode, a normal natural electric potential was obtained and it was found that a normal measurement became possible again.

Figure 12:
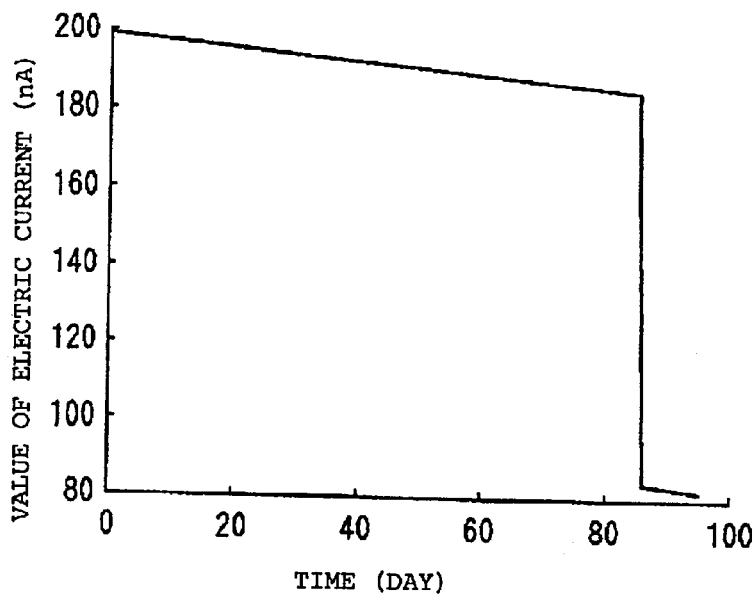
FIG. 12 shows an output change vs. time of a sensor evaluated in the example.

On the other hand, in the sensor without having the examining electrode and the spare reference electrode, it was impossible to confirm whether a normal measurement was possible or not. After 85 days an electric current value indicating an output of the sensor decreased suddenly and a normal measurement of glucose became impossible. In FIG. 12 the results of the measured output (electric current values) changes vs. time are shown.

Reference Example 1

The effects of interfering substances on an electric potential of a reference electrode were measured. The sensors used for the measurement are:

(i) The sensor as used in Example 1 (a sensor provided with a diffusion-limiting layer made of polymethacrylic acid 1H, 1H-perfluorooctyl).

(ii) A sensor without having a diffusion-limiting layer (a sensor has a similar structure as used in (i) except for having no diffusion-limiting layer)

A sample to be measured was a buffer solution of pH7 TES (N-tris(hydroxymethyl)-methyl-2-aminoethanesulfonic acid) containing 1 mM of an interfering substance and 150 mM of sodium chloride. The interfering substances were (a) potassium sulfide, (b) potassium bromide and (c) potassium iodide.

At beginning the sample did not contain the interfering substance. After about 13 to 20 sec the interfering substance was added.

Figure 13:
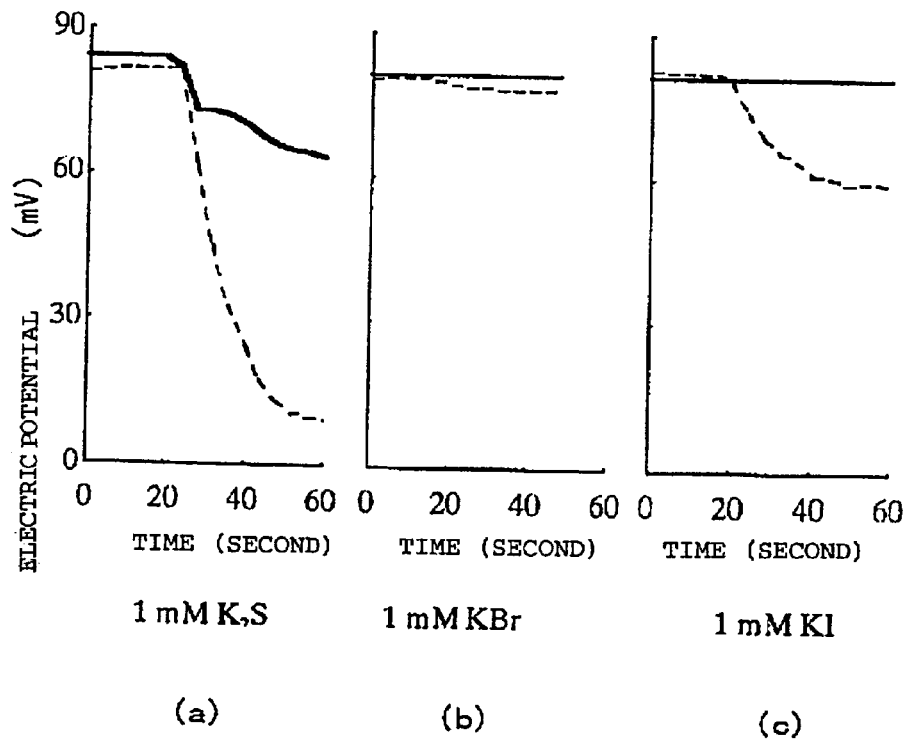
FIGS. 13(a)–13(c) shows effects of interfering substances on an electric potential of a reference electrode.

As shown in FIGS. 13(a)–13(c), an electrode potential in the sensor (ii) having no diffusion-limiting layer is greatly reduced by adding the interfering substance. On the other hand, it can be seen that a change of the electrode potential in the sensor (i) having the diffusion-limiting layer is controlled.

Reference Example 2

In this example, a change of a sensor output and a reference electrode potential vs. time was measured using a measuring sample of a 100 mg/dl glucose solution containing 1 mM (end concentration) of potassium sulfide as an interfering substance. The sensor used in the measurement was the same sensor (a sensor provided with a diffusion-limiting layer made of polymethacrylic acid 1H, 1H-perfluorooctyl) as used in Example 1.

The results of the measurement are shown in 15(a)–15(b). At first, the measured sample was a glucose solution that did not contain potassium sulfide and at the time indicated by an arrow 1 mM of potassium sulfide was added. A sensor output and a reference electrode potential were changed by adding such a high concentration of an interfering substance. After the addition of the interfering substance the sensor still indicated the output but the value of the output continued to decrease as time elapsed.

As shown in FIG. 5, when a reference electrode has been damaged, the output of the sensor reduces greatly and therefore the abnormality in the sensor may sometimes be recognized even if the abnormality in the reference electrode itself cannot be detected. However, when the sensor indicates some output as shown in this Reference Example 2, it is hard to recognize the abnormality in the sensor. In other words, when the natural potential of the reference electrode deviates from a normal value even if the reference electrode is not damaged, a conventional sensor keep measuring without detecting the abnormality as if the reference electrode were functioning normally which causes a reduction in the accuracy of the measurement.

On the other hand, since the electrochemical sensor having an examining electrode of this invention can detect a small change of the electric potential of the reference electrode, it is possible to tell the replacement time of the reference electrode accurately and, therefore, to increase the reliability of the measured value.

What is claimed is:

1. An electrochemical sensor, comprising:

a working electrode a counter electrode;

a reference electrode;

means for examining the reference electrode for examining an electric potential of the reference electrode;

an immobilized enzyme layer formed at least on the working electrode; and a diffusion-limiting layer comprising fluoroalcohol ester of polycarboxylic acid, which covers at least the working electrode and the reference electrode, and is formed on the immobilized enzyme layer.

2. An electrochemical sensor, comprising:
a working electrode;
a counter electrode;
a reference electrode;
means for examining the reference electrode for examining an electric potential of the reference electrode;
a spare reference electrode for use in place of the reference electrode when the means for examining the reference electrode detects an abnormal electric potential of the reference electrode; and
an immobilized enzyme layer formed at least on the working electrode.

3. The electrochemical sensor as claimed in claim 2, further comprising:
a diffusion-limiting layer comprising fluoroalcohol ester of polycarboxylic acid, which covers at least the working electrode and the reference electrode, and is formed on the immobilized enzyme layer.

4. The electrochemical sensor as claimed in claim 2, further comprising:
means for switching the reference electrode by which the spare reference electrode is used in place of the reference electrode when the abnormal electric potential is detected by the means for examining the reference electrode.

5. The electrochemical sensor as claimed in in claim 4, further comprising:
a diffusion-limiting layer comprising fluoroalcohol ester of polycarboxylic acid, which covers at least the working electrode and the reference electrode, and is formed on the immobilized enzyme layer.

6. The electrochemical sensor as claimed in claim 2, further comprising:
means for informing to inform of the time of replacing the reference electrode when the abnormal electric potential is detected by the means for examining the reference electrode.

7. The electrochemical sensor as claimed in claim 6, further comprising:
a diffusion-limiting layer comprising fluoroalcohol ester of polycarboxylic acid, which covers at least the working electrode and the reference electrode, and is formed on the immobilized enzyme layer.

8. The electrochemical sensor as claimed in claim 6, further comprising:
means for switching the reference electrode by which the spare reference electrode is used in place of the reference electrode when the abnormal electric potential is detected by the examining measures of the reference electrode.

9. The electrochemical sensor as claimed in claim 8, further comprising:
a diffusion-limiting layer comprising fluoroalcohol ester of polycarboxylic acid, which covers at least the working electrode and the reference electrode, and is formed on the immobilized enzyme layer.

10. An electrochemical sensor, comprising:
a working electrode;
a counter electrode;
a reference electrode; and
means for examining the reference electrode for examining an electric potential of the reference electrode,
wherein the means for examining the reference electrode comprises an examining electrode which is use as a standard to measure the electric potential of the reference electrodes and a measuring apparatus by which a potential difference between the examining electrode and the reference electrode is measured.

11. The electrochemical sensor as claimed in claim 10, further comprising:
an immobilized enzyme layer is formed at least on the working electrode.

12. The electrochemical sensor as claimed in claim 11, further comprising:
a diffusion-limiting layer comprising fluoroalcohol ester of polycarboxylic acid, which covers at least the working electrode and the reference electrode, and is formed provided on the immobilized enzyme layer.

13. The electrochemical sensor as claimed in claim 10, further comprising:
a spare reference electrode for use in place of the reference electrode when the means for examining the reference electrode detects an abnormal electric potential of the reference electrode.

14. The electrochemical sensor as claimed in claim 13, further comprising:
an immobilized enzyme layer formed at least on the working electrode.

15. The electrochemical sensor as claimed in claim 14, further comprising:
a diffusion-limiting layer comprising fluoroalcohol ester of polycarboxylic acid, which covers at least the working electrode and the reference electrode, and is formed on the immobilized enzyme layer.

16. The electrochemical sensor as claimed in claim 13, further comprising:
means for switching the reference electrode by which the spare reference electrode is used in place of the reference electrode when the abnormal electric potential is detected by the means for examining the reference electrode.

17. The electrochemical sensor as claimed in claim 16, further comprising:
an immobilized enzyme layer formed at least on the working electrode.

18. The electrochemical sensor as claimed in claim 17, further comprising:
a diffusion-limiting layer comprising fluoroalcohol ester of polycarboxylic acid, which covers at least the working electrode and the reference electrode, and is formed on the immobilized enzyme layer.

19. The electrochemical sensor as claimed in claim 13, further comprising:
means for informing to inform of the time of replacing the reference electrode when the abnormal electric potential is detected by the means for examining the reference electrode.

20. The electrochemical sensor as claimed in claim 19, further comprising:
an immobilized enzyme layer is formed at least on the working electrode.

21. The electrochemical sensor as claimed in claim 20, further comprising:
a diffusion-limiting layer comprising fluoroalcohol ester of polycarboxylic acid, which covers at least the working electrode and the reference electrode and is formed on the immobilized enzyme layer.

22. The electrochemical sensor as claimed in claim 19, further comprising:

means for switching the reference electrode by which the spare reference electrode is used in place of the reference electrode when the abnormal electric potential is detected by the means for examining the reference electrode.

23. The electrochemical sensor as claimed in claim 22, further comprising:

an immobilized enzyme layer formed at least on the working electrode.

24. The electrochemical sensor as claimed in claim 23, further comprising:

a diffusion-limiting layer comprising fluoroalcohol ester of polycarboxylic acid, which covers at least the working electrode and the reference electrode, and is formed on the immobilized enzyme layer.

25. An electrochemical sensor comprising:

a working electrode;

a counter electrode;

a reference electrode;

a spare electrode for use in place of the reference electrode when a use of the reference electrode is stopped;

an immobilized enzyme layer formed at least on the working electrode; and a diffusion-limiting layer comprising fluoroalcohol ester of polycarboxylic acid, which covers at least the working electrode and the reference electrode, and is formed on the immobilized enzyme layer.

26. An electrochemical sensor comprising:

a working electrode;

a counter electrode;

a reference electrode;

a spare electrode for use in place of the reference electrode when a use of the reference electrode is stopped;

means for switching the reference electrode by which the spare reference electrode is used in place of the reference electrode when the use of the reference electrode is stopped; and an immobilized enzyme layer is formed at least on the working electrode.

27. The electrochemical sensor as claimed in claim 26, further comprising:

a diffusion-limiting layer comprising fluoroalcohol ester of polycarboxylic acid, which covers at least the working electrode and the reference electrode, and is formed on the immobilized enzyme layer.

* * * * *